United States Patent [19]

Berchem et al.

[11] Patent Number: 5,150,304
[45] Date of Patent: Sep. 22, 1992

[54] METHOD OF MAKING AN IMPLANTABLE JOINT PROSTHESIS

[75] Inventors: Rütger Berchem, Essen; Volkhard Schnitzler, Bochum, both of Fed. Rep. of Germany

[73] Assignee: Metalpraecis Berchem+Schaberg Gesellschaft fur Metallformgebung mbH, Gelsenkirchen, Fed. Rep. of Germany

[21] Appl. No.: 603,632

[22] Filed: Oct. 25, 1990

[30] Foreign Application Priority Data

Oct. 28, 1989 [EP] European Pat. Off. ........... 89120072

[51] Int. Cl.⁵ ...................... G06F 15/46; A61F 2/30
[52] U.S. Cl. .................................. 364/474.24; 623/18
[58] Field of Search ............. 364/468, 474.24, 413.28, 364/518, 521, 413.01, 413.13, 413.14; 623/18-23; 395/161

[56] References Cited

U.S. PATENT DOCUMENTS

| | | | |
|---|---|---|---|
| 4,536,894 | 8/1985 | Galante et al. | 623/18 X |
| 4,611,288 | 9/1986 | Duret et al. | 364/413.28 |
| 4,619,659 | 10/1986 | Witzel | 623/23 |
| 4,663,720 | 5/1987 | Duret et al. | 364/413.28 |
| 4,702,930 | 10/1987 | Heide et al. | 623/18 X |
| 4,742,464 | 5/1988 | Duret et al. | 364/474.24 X |
| 4,742,473 | 5/1988 | Shugar et al. | 364/521 X |
| 4,936,862 | 1/1990 | Walker et al. | 364/468 X |
| 5,035,718 | 7/1991 | Berchem | 623/18 |

FOREIGN PATENT DOCUMENTS 3740438 6/1989 Fed. Rep. of Germany.

OTHER PUBLICATIONS

McGraw-Hill Encyclopedia of Science & Technology, pp. 409, 410; date unknown.

Primary Examiner—Joseph Ruggiero
Attorney, Agent, or Firm—Herbert Dubno

[57] ABSTRACT

A method of making a joint implant prosthesis which has a shaft adapted to fit into the bone cavity of a tubular bone and having a core region and a shaft region. The geometry of the bone cavity is determined by an irradiation method and based upon the detected geometry, the shaft is dimensioned. First a geometric centroid axis of the bone passage is determined and then the core region built up by computer around this axis with the aid of finite element analysis based upon geometry of the bone cavity. The boundary conditions of an undercut-free shaft and uniform distribution of the normal stresses in the shaft bone transition region are observed. The second boundary condition is also used as a control in the coating of the core with synthetic bone material and in the configuration of the surface region.

15 Claims, 2 Drawing Sheets

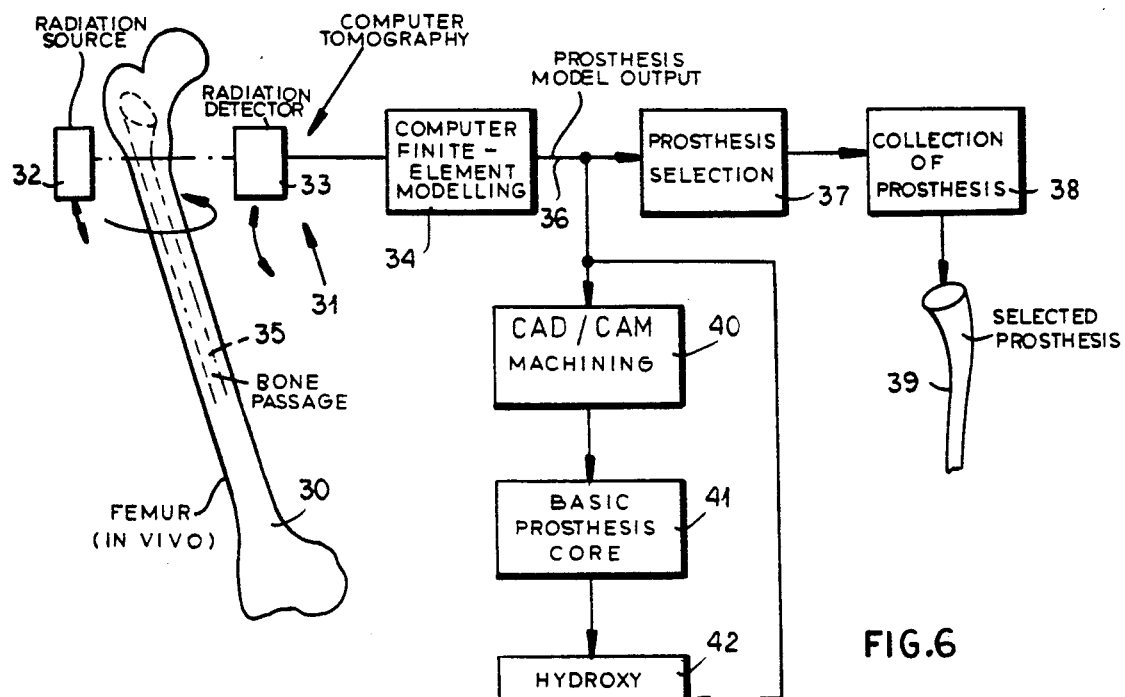
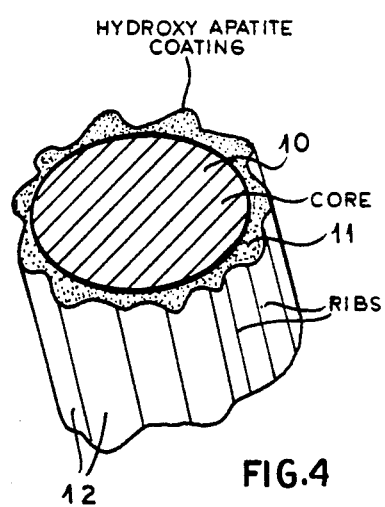
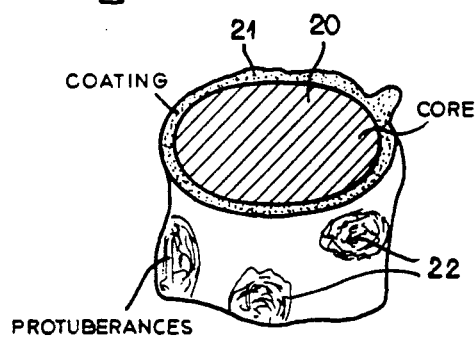

METHOD OF MAKING AN IMPLANTABLE JOINT PROSTHESIS

CROSS REFERENCE TO RELATED APPLICATION

This application is related to the commonly owned copending application Ser. No. 07/436,323, U.S. Pat. No. 5,035,718 which, in turn, is related to earlier applications which have matured into U.S. Pat. Nos. 4,946,379 and 4,955,912.

FIELD OF THE INVENTION

Our present invention relates to a method for producing an implantable joint prosthesis which has a shaft which can be seated in a bone cavity of a tubular bone such as, for instance, the femur where the joint is a hip joint as is the case with the above-mentioned patent and patent applications.

BACKGROUND OF THE INVENTION

It is known to provide joint prostheses having shafts adapted to be received in the bone cavity of a bone of a particular individual by ascertaining the geometry of that bone cavity and fabricating an individual prosthesis to fit the cavity. In general, these techniques have used a modification of a surface region of a shaft having a relatively large core filling most of the cross section of the joint cavity.

In German Patent Document DE-OS 37 40 438 and in the copending application mentioned above, a preformed shaft is described which is coated with a bone replacement or synthetic bone material, e.g. hydroxyapatite.

This coating can be applied in accordance with the geometry of the bone passage and the coating of the synthetic bone material can be of substantially greater thickness in the loading regions than is the case in regions of reduced loading.

Where the regions of greater loading lie for a particular patient in whom the joint prosthesis is to be implanted, can be determined without considerable effort utilizing X-ray imaging and with the aid of modern computer-supported mechanics. For example, computer tomography, which has been quite common of late in medicine, may be used to advantage for this purpose. The preformed shaft can be a serial or mass-produced product whose geometry follows average values for particular bones. For example, from a number of such shafts for differing bone sizes, a relatively good fitting shaft can be selected.

Of course, it is also possible to form the shaft individually, i.e. in accordance with measurements of the inner periphery and the cross section of the bone cavity into which the shaft is to be inserted.

Notwithstanding the efforts made heretofore, it has been found that singular stress regions arise in joint prostheses made by earlier methods and even utilizing the coated shaft of the above-identified applications and patents.

OBJECTS OF THE INVENTION

It is the principal object of the present invention to provide an improved method of making an implantable joint prosthesis which can rovide improved prothesis shafts not only from the point of of view of the geometry of the bone passage, but also can ensure an extremely uniform distribution of the stresses.

Another object of the invention is to provide an improved method of forming an implant whereby drawbacks of earlier systems are avoided.

SUMMARY OF THE INVENTION

These objects and others which will become apparent hereinafter are attained, in accordance with the invention, by scanning the bone in which the implant is to be inserted to ascertain the geometry of the bone cavity, from the data thus obtained from the scan, determining the lie of the geometric centroidal axis of the geometry of the bone cavity thus obtained and, after the shaft core shape surrounding that axis has been determined by finite element analysis based upon the geometry of the cavity, utilizing the boundary conditions that the shaft configuration should be free from undercuts and that there should be a uniform stress distribution in the transition region between shaft and bone for the normal stresses to be taken up by the implanted prosthesis, the surface region is formed.

The geometrical centroid axis connects the centroids or centers of gravity of successive cross sections of the cavity along an axis. The freedom from undercuts ensures that the implant joint prosthesis according to the invention can be inserted without difficulty.

More particularly, the method of the invention can comprise the steps of:

(a) ascertaining the geometry of a bone cavity in a bone adapted to receive an implantable joint prosthesis by scanning the bone by irradiation;

(b) determining a lie of a geometrical centroid axis from the geometry ascertained in step (a);

(c) developing a shaft core region extending along the axis by finite element analysis of the geometry with the boundary conditions
 ($c_1$) that a shaft core formed by the region along the axis must have an undercut-free configuration, and
 ($c_2$) that there must be a uniform stress distribution along the shaft of normal stresses arising in a shaft/bone transition region;

(d) establishing a configuration of a surface region on the core considering condition ($c_1$) and in accordance with the result of condition ($c_2$); and (e) fabricating a shaft of an implantable joint prosthesis with the core and the surface region.

The implantable joint prosthesis is an elongated load-bearing member not unlike a beam or truss and, indeed, in conjunction with the bone in which it is to be received, forms a complex load-bearing element.

From the configuration and dimensions of a load-bearing element, the stress distribution can be determined by the application of conventional mechanics.

Occasionally it is also necessary, at predetermined points of the load-bearing structure, to calculate the shifts in the sense of classical mechanics, in order to estimate whether predetermined mechanical values may be exceeded. The stress distribution must be compatible, namely, the requirements for equilibrium between internal and external forces must be satisfied.

The invention is based upon our recognition that this compatibility is required also for implant joint prostheses. For a given set of dimensions of a system of stresses and deformations, initially in practice the basic equations for these relationships must be ascertained and the equilibrium and compatibility requirements must satisfy these equations. As a rule, however, it is difficult to calculate the equations for a geometry, loading and material conditions used in the formation of joint prostheses. In the past, certain inaccuracies had to be accepted.

By contrast, the invention utilizes modern electronic computer systems which have greatly enlarged the scope of such calculations and improved upon them. Such computers have made numerical solutions possible and have allowed finite element analysis to be used for the first time in the construction of joint prostheses.

The basic concept of this method is the modelling of a continuum from an assembly of partial regions referred to as finite elements. In each partial region, the relationship between the stresses and shifts can be described as a set of function statements.

These sets of statements are limited by the boundary conditions set forth, namely, that the shaft configuration should be free from undercuts and that there should be a uniform stress distribution of the normal stresses taken up by the implant prosthesis in the shaft-bone transition regions. Under these circumstances, differently stressed regions are eliminated and the stress distribution allows differing thicknesses of coating of the synthetic bone material until there is stress equalization.

Specifically, the uniform stress distribution can be obtained by providing the surface region with projecting ribs or protuberances or both. The surface region can, in addition, or alternatively, be formed as a coating of synthetic bone material, usually hydroxy apatite. Surprisingly, it is possible to obtain in this manner a very homogeneous uniform stress distribution which appears to be a result of the fact that the geometric centroid axis is first determined and the core portion of the shaft developed around and along this axis.

BRIEF DESCRIPTION OF THE DRAWING

The above and other objects, features and advantages of the present invention will become more readily apparent from the following description, reference being made to the accompanying drawing in which:

FIG. 4 is a cross sectional view of the shaft of the prosthesis showing the coating provided with ribs;

FIG. 5 is a cross sectional view of the shaft of the prosthesis showing the coating provided with protuberances; and FIG. 6 is a block diagram illustrating the principles of the invention.

SPECIFIC DESCRIPTION

Figures 1, 2, 3:
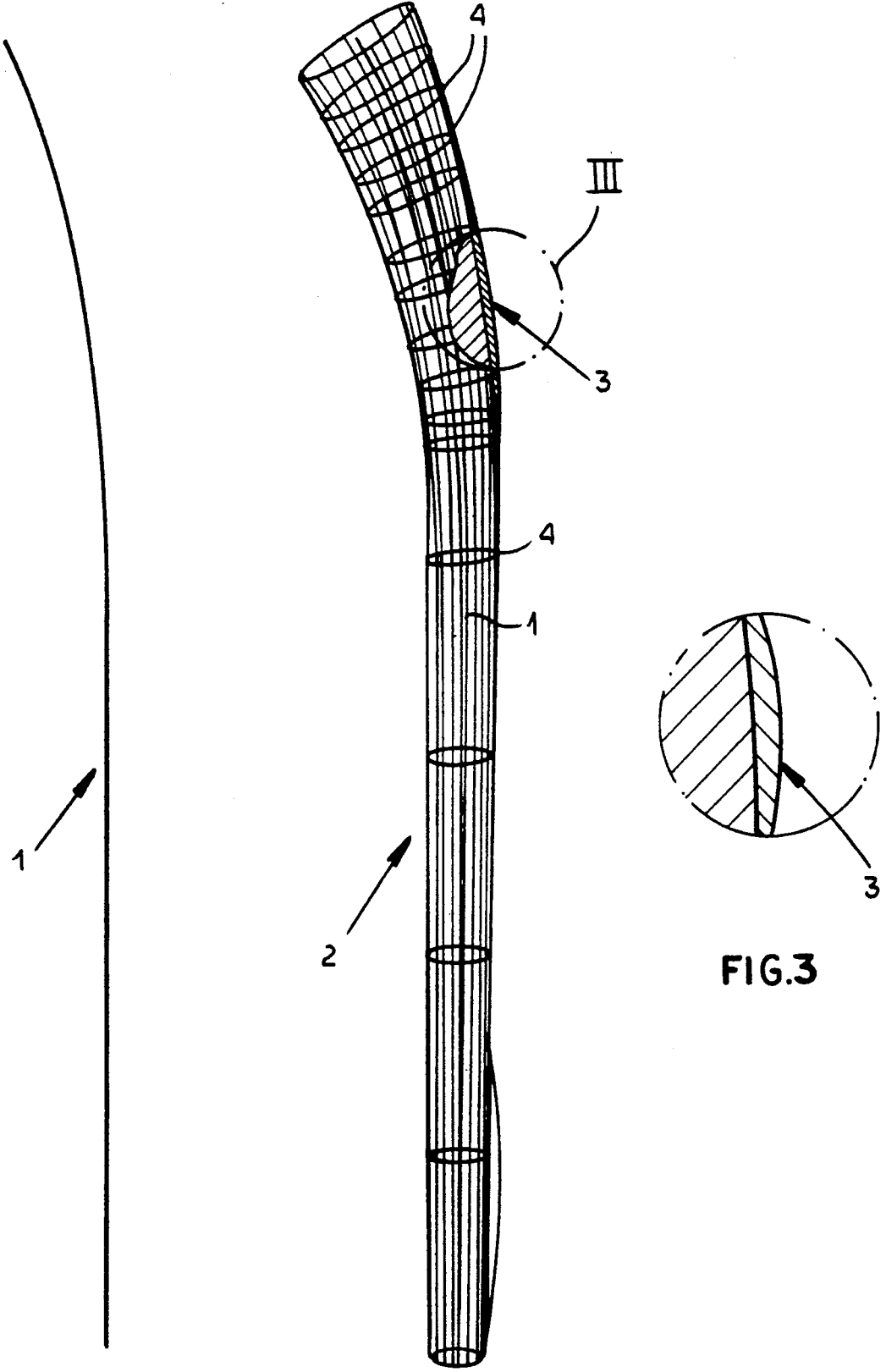
FIG. 1 is an illustration of the geometric centroid line or axis of a femur prosthesis and its bone cavity.
FIG. 2 is an elevational view of the shaft of a joint implant prosthesis partly in section and without the application of the ball or collar as described, for example, in the aforementioned copending application and its parent patent.
FIG. 3 is an enlarged cross sectional view of the region III of FIG. 2.

The invention is described in connection with the formation of an individual joint implant prosthesis for a hip joint. Utilizing the described data processing, the geometry of the bone cavity in the shaft of the femur is determined. From this analysis of the geometry of the cavity, the geometric centroid line or axis 1 is ascertained.

The curvature of this line can, of course, be more complex than that illustrated. For example, it may also be curved out of or into the plane of the paper and can have a multiple curvature in any plane. What is important to realtize, of course, is that the curvature while not great, may vary widely for the individual joint prosthesis and the orientation or lie of the centroid line will influence the seating of the joint and the retention and load-supporting properties of the prosthesis.

FIG. 2 shows the shaft 2 which is developed around the axis 1 utilizing finite element analysis in the manner described. For illustration, we have shown ring-shaped transverse curves 4 which correspond to cross sectional planes through the femur and the intersection of the cavity wall with these planes.

Each of the circles thus surrounds a plane Figure or area which has a centroid or center of curvature, through which the axis 1 passes.

Stated otherwise, the geometric centroid line 1 passes through all of the centroids of these intersection planes and thus the areas bounded by the transverse curves.

The enlarged cross section of FIG. 3 shows the configuration of a surface region 3 which, according to the invention is optimized as to the stress distribution.

Utilizing the data processing and calculations with modern computer technologies automatically, we are able to ensure a uniform stress distribution all along the shaft of the implant.

While it is preferred, in accordance with the invention, to fabricate the shaft and effect the coating automatically on an individual basis for the particular femur, it will be apparent that a supply of implant prostheses fabricated to fit femurs of different sizes and structure can be provided in various sizes and shapes so that the selection of a preformed implant by the physician from a large number of these prefabricated units can be computer facilitated or can be automatic as well so that the delay in fabrication can be avoided.

Referring to FIG. 4, it can be seen that the core 10 of the shaft of the prosthesis can be surrounded by the coating 11 of synthetic bone material, e.g. hydroxyapatite, and that this region can have ribs 12 which project to engage the wall of the cavity. Alternatively or in addition, the core 20 may have a coating 21 of the synthetic bone material formed with protuberances 22.

Turning now to FIG. 6, in which the method is illustrated in greater detail, we see that a femur 30 prior to surgery and truncation of the femur head can be scanned by computer tomography represented at 31, e.g. with a radiation source 32, for example an X-ray source, and a radiation detector 33 to provide the information necessary for the computer 34 to model the bone cavities 35 by first ascertaining the centroid axis and then modelling the core of the shaft therearound.

With the prosthesis model output 36 from the computer, we can proceed to automatic prosthesis selection at 37 in which the model is compared with stored data representing a variety of sizes and shapes of prostheses maintained in a collection 38. Upon a match, the physician may be signalled to allow him to withdraw the desired prosthesis shaft 39 from the collection or the location and outputting of the prosthesis from an appropriate magazine may be effected automatically. Each of the prostheses 39, of course, would have been machined, based upon the circumstances and boundary conditions outlined previously.

Alternatively, the prosthesis model output 36 may be fed to a computer-associated design/computer-associated machining unit 40, for example, a functional five-axis CAM machining tool and in which the basic prosthesis core is formed. The core 41 is then coated with hydroxy apatite at 42 under control of the model generated by the computer 34 to provide the individually generated prosthesis 43.

We claim:

1. A method of making an implantable joint prosthesis, comprising the steps of:
   (a) ascertaining the geometry of a bone cavity in a bone adapted to receive an implantable joint prosthesis by scanning said bone by irradiation;
   (b) determining a lie of a geometrical centroid axis from the geometry ascertained in step (a);
   (c) developing a shaft core region extending along said axis by finite element analysis of said geometry with the boundary conditions
      ($c_1$) that a shaft core formed by said region along said axis must have an undercut-free configuration, and
      ($c_2$) that there must be a uniform stress distribution along said shaft of normal stresses arising in a shaft/bone transition region;
   (d) establishing a configuration of a surface region on said core considering condition ($c_1$) and in accordance with the result of condition ($c_2$); and
   (e) fabricating a shaft of an implantable joint prosthesis with said core and said surface region.

2. The method defined in claim 1 wherein said transition region is formed by applying a coating of a synthetic bone material to said core of said shaft.

3. The method defined in claim 2 wherein said surface region is formed with projecting ribs.

4. The method defined in claim 2 wherein said surface region is formed with projections distributed thereover.

5. The method defined in claim 1 wherein said surface region is formed with projecting ribs.

6. The method defined in claim 1 wherein said surface region is formed with projections distributed thereover.

7. A method of making an implantable joint prosthesis, comprising the steps of:
   (a) ascertaining the geometry of a bone cavity in a bone adapted to receive an implantable joint prosthesis by scanning said bone by irradiation;
   (b) determining a lie of a geometrical centroid axis from the geometry ascertained in step (a);
   (c) developing a shaft core region extending along said axis by finite element analysis of said geometry with the boundary conditions
      ($c_1$) that a shaft core formed by said region along said axis must have an undercut-free configuration, and
      ($c_2$) that there must be a uniform stress distribution along said shaft of normal stresses arising in a shaft/bone transition region;
   (d) establishing a configuration of a surface region on said core considering condition ($c_1$) and in accordance with the result of condition ($c_2$); and
   (e) selecting from a collection of implantable joint shafts a shaft of an implantable joint prosthesis for said bone with said core and said surface region.

8. The method defined in claim 7 wherein said transition region is formed by applying a coating of a synthetic bone material to said core of said shaft.

9. The method defined in claim 8 wherein said surface region is formed with projecting ribs.

10. The method defined in claim 8 wherein said surface region is formed with projections distributed thereover.

11. The method defined in claim 7 wherein said surface region is formed with projecting ribs.

12. The method defined in claim 7 wherein said surface region is formed with projections distributed thereover.

13. A method of forming a joint prosthesis implant, comprising the steps of:
   (a) ascertaining the geometry of a bone cavity in a bone adapted to receive an implantable joint prosthesis by scanning said bone by irradiation;
   (b) determining a lie of a geometrical centroid axis from the geometry ascertained in step (a);
   (c) developing a shaft core region extending along said axis by finite element analysis;
   (d) establishing a configuration of a surface region on said core by applying a coating of a synthetic bone material thereto in response to said geometry and said analysis and configured to provide, on implantation, a uniform stress distribution for normal stresses in a bone/shaft transition region; and
   (e) implanting the shaft provided with said coating in said cavity.

14. The method defined in claim 13 wherein said surface region is formed with projecting ribs.

15. The method defined in claim 13 wherein said surface region is formed with projections distributed thereover.

* * * * *